United States Patent
Jiang et al.

(10) Patent No.: US 11,160,824 B2
(45) Date of Patent: Nov. 2, 2021

(54) APPLICATION OF LNCRNAS ENST00000607393 SIRNA IN PREPARING PREPARATION FOR TREATING GLAUCOMA

(71) Applicant: THE SECOND XIANGYA HOSPITAL OF CENTRAL SOUTH UNIVERSITY, Hunan (CN)

(72) Inventors: Bing Jiang, Hunan (CN); Lili Xie, Hunan (CN); Lusi Zhang, Hunan (CN); Wei Huang, Hunan (CN)

(73) Assignee: THE SECOND XIANGYA HOSPITAL OF CENTRAL SOUTH UNIVERSITY, Hunan (CN)

( * ) Notice: Subject to any disclaimer, the term of this patent is extended or adjusted under 35 U.S.C. 154(b) by 83 days.

(21) Appl. No.: 16/618,400

(22) PCT Filed: May 25, 2018

(86) PCT No.: PCT/CN2018/088323
§ 371 (c)(1),
(2) Date: Dec. 2, 2019

(87) PCT Pub. No.: WO2018/223847
PCT Pub. Date: Dec. 13, 2018

(65) Prior Publication Data
US 2020/0289544 A1 Sep. 17, 2020

(30) Foreign Application Priority Data
Jun. 7, 2017 (CN) .......................... 201710423727.4

(51) Int. Cl.
*A61K 31/7105* (2006.01)
(52) U.S. Cl.
CPC .............................. *A61K 31/7105* (2013.01)

(58) Field of Classification Search
CPC ........ C12Q 2600/158; C12Q 2600/178; C12Q 1/6883; A61K 31/7105
See application file for complete search history.

(56) References Cited

U.S. PATENT DOCUMENTS 9,526,799 B2  12/2016  Chatterton

FOREIGN PATENT DOCUMENTS

| CN | 105002182 | 10/2015 |
| CN | 106978509 | 7/2017 |
| CN | 107028972 | 8/2017 |

OTHER PUBLICATIONS

Xie et al. (The American Journal of Pathology, 2019 vol. 189:739-752).*

(Continued)

*Primary Examiner* — Terra C Gibbs
(74) *Attorney, Agent, or Firm* — JCIP Global Inc.

(57) ABSTRACT

The present invention provides an application of lncRNAs ENST00000607393 siRNA in preparing a preparation for treating glaucoma. The present invention clarifies the correlation between the expression level of ENST00000607393 and the calcification of human primary trabecular meshwork cells. The expression level of ENST00000607393 in human primary trabecular meshwork cells is firstly down-regulated to 46.21% of a control group by siRNA interference. Under the condition of intervening with the cells by a 500 µmol/L hydrogen peroxide solution for 48 hours, it is observed that compared with the control group, the down-regulation of ENST00000607393 expression can significantly decrease the ALP activity in human primary trabecular meshwork cells, and thus significantly decrease the calcification level of human primary trabecular meshwork cells to play a role of treating or preventing glaucoma.

3 Claims, 10 Drawing Sheets
(4 of 10 Drawing Sheet(s) Filed in Color)
Specification includes a Sequence Listing.

(56) References Cited

OTHER PUBLICATIONS

"International Search Report (Form PCT/ISA/210) of PCT/CN2018/088323", dated Jul. 31, 2018, with English translation thereof, pp. 1-5.

* cited by examiner

APPLICATION OF LNCRNAS ENST00000607393 SIRNA IN PREPARING PREPARATION FOR TREATING GLAUCOMA

CROSS-REFERENCE TO RELATED APPLICATION

This application is a 371 of international application of PCT application serial no. PCT/CN2018/088323, filed on May 25, 2018, which claims the priority benefit of China application no. 201710423727.4, filed on Jun. 7, 2017. The entirety of each of the above mentioned patent applications is hereby incorporated by reference herein and made a part of this specification.

BACKGROUND OF THE INVENTION

1. Technical Field

The present invention belongs to the technical field of molecular therapy, and in particular relates to application of lncRNAs ENST00000607393 SiRNA in preparation of a preparation for treating glaucoma.

2. Background Art

Glaucoma is the first irreversible blindness-causing eye disease in the world and the most common optic neuropathy. At present, the diagnosis of glaucoma mainly depends on medical history, and changes in morphology and function. The main treatment measure is still to control intraocular tension. The glaucoma-related serological screening, biochemical examination and detection standards are still in a relatively blank state. Therefore, it is especially important to find a high-sensitivity and high-specificity marker for diagnosis and monitoring of glaucoma. In recent years, with the development of high-throughput sequencing, gene chip and other technologies, the importance of "dark matter" such as non-coding RNA (ncRNA) has become more prominent. Among them, ncRNA can be divided into a small non-coding RNA (sncRNA) (<200 bp) and a long non-coding RNA (lncRNA) (>200 bp) according to the length thereof. Research has shown that the mammalian genome can encode tens of thousands of lncRNAs, of which about 40% of lncRNAs are specifically expressed in the brain and involved in the regulation of gene expression in the physiological and pathological activities of the brain nervous system. Moreover, the abnormal expression of specific lncRNAs is closely related to the occurrence and development of glaucoma. Therefore, glaucoma-related lncRNAs research is expected to fill the gap in glaucoma-related biochemical detection.

lncRNA is highly conserved and tissue-specific, and is abundant in the brain. lncRNA not only participates in the growth and development and function perfection of the nervous system to make the nervous system grow and develop according to a certain time sequence in a certain space, but also participates in executing the function of the nervous system. lncRNA participates in the development and function execution of the nervous system through various mechanisms, including gene imprinting, chromatin remodeling, cell cycle regulation, splicing regulation, mRNA degradation and translational regulation and other processes as a cis-acting element and a trans-acting factor. For example, microRNAs (miRNAs) have been shown to be involved in many aspects of the body's physiological and pathological activities. RaniN et al. found that specific lncRNAs molecules could be mediated by miRNA to regulate a Notch pathway, thereby achieving the regulating effect on neurodevelopment. In addition, the abnormal expression of lncRNAs is closely related to the pathological state of the nervous system. Tan J Y et al. demonstrated that the abnormal expression of long non-coding RNA SCA7 (lnc-SCA7) could be mediated by miR-124 to affect the expression of a gene SCA7 at the post-transcriptional level, causing hereditary spinocerebellar ataxia 7. This lesion is mainly characterized by degeneration of the retina and cerebellar neurons. Therefore, it is a feasible means to reflect the physiological and pathological states of the nervous system by detecting changes in the composition and expression level of lncRNAs, and then achieve the purpose of treating diseases by regulating the expression of lncRNAs.

Pathological calcification of trabecular meshwork cells is one of the important pathological characteristics of glaucoma. Research proves that the trabecular meshworks of patients with glaucoma have a higher hardness than people in a control group. As an important component of an aqueous humor outflow channel, the state of the trabecular meshwork can have a direct impact on intraocular tension. Research has shown that the hardness of trabecular meshwork may be an important determinant of optic nerve damage in patients with glaucoma. Therefore, it is of great significance to find novel lncRNA molecules related to trabecular meshwork calcification for future glaucoma-related therapies.

SUMMARY OF THE INVENTION

Technical Problems

The present invention aims to provide application of lncRNAs ENST00000607393 SiRNA in preparation of a preparation for treating glaucoma, which is of great significance for the treatment of glaucoma.

Problem Solution

Technical Solution

SUMMARY OF THE INVENTION

Application of lncRNAs ENST00000607393 SiRNA in preparation of a preparation for treating glaucoma is provided. The sequence of lncRNAs ENST00000607393 is shown in SEQ ID NO: 1.

The preparation for treating glaucoma includes: a positive-sense strand sequence of 5'-GCAGGCGUGUG-CAUUUCUU-3' (SEQ ID NO: 2), and an antisense strand sequence of 5'-AAGAAAUGCACACGCCUGC-3' of the siRNA against ENST00000607393 (SEQ ID No: 3).

The preparation for treating glaucoma further includes: a positive-sense strand sequence of 5'-UUCUCCGAACGU-GUCACGU-3' (SEQ ID NO: 4), and an antisense strand sequence of 5'-ACGUGACACGUUCGGAGAA-3' (SEQ ID NO: 5) of a negative control.

Beneficial Effects of the Invention

Beneficial Effects

The present invention clarifies the correlation between the expression level of ENST00000607393 and the calcification of human primary trabecular meshwork cells. The expression level of ENST00000607393 in human primary trabecular meshwork cells is firstly down-regulated to 46.21% of a control group by siRNA interference. Under the condition of intervening with the cells by a 50 µmol/L hydrogen peroxide solution for 48 hours, it is observed that compared with the control group, the down-regulation of ENST00000607393 expression can significantly decrease the ALP activity in human primary trabecular meshwork cells to play a role of treating or preventing glaucoma.

BRIEF DESCRIPTION OF THE DRAWINGS

Description of the drawings. The invention contains at least one color photograph. Copies of the disclosure publication with the color photographs will be provided by the Patent & Trademark Office upon request and payment of the necessary fee.

Figure 1:
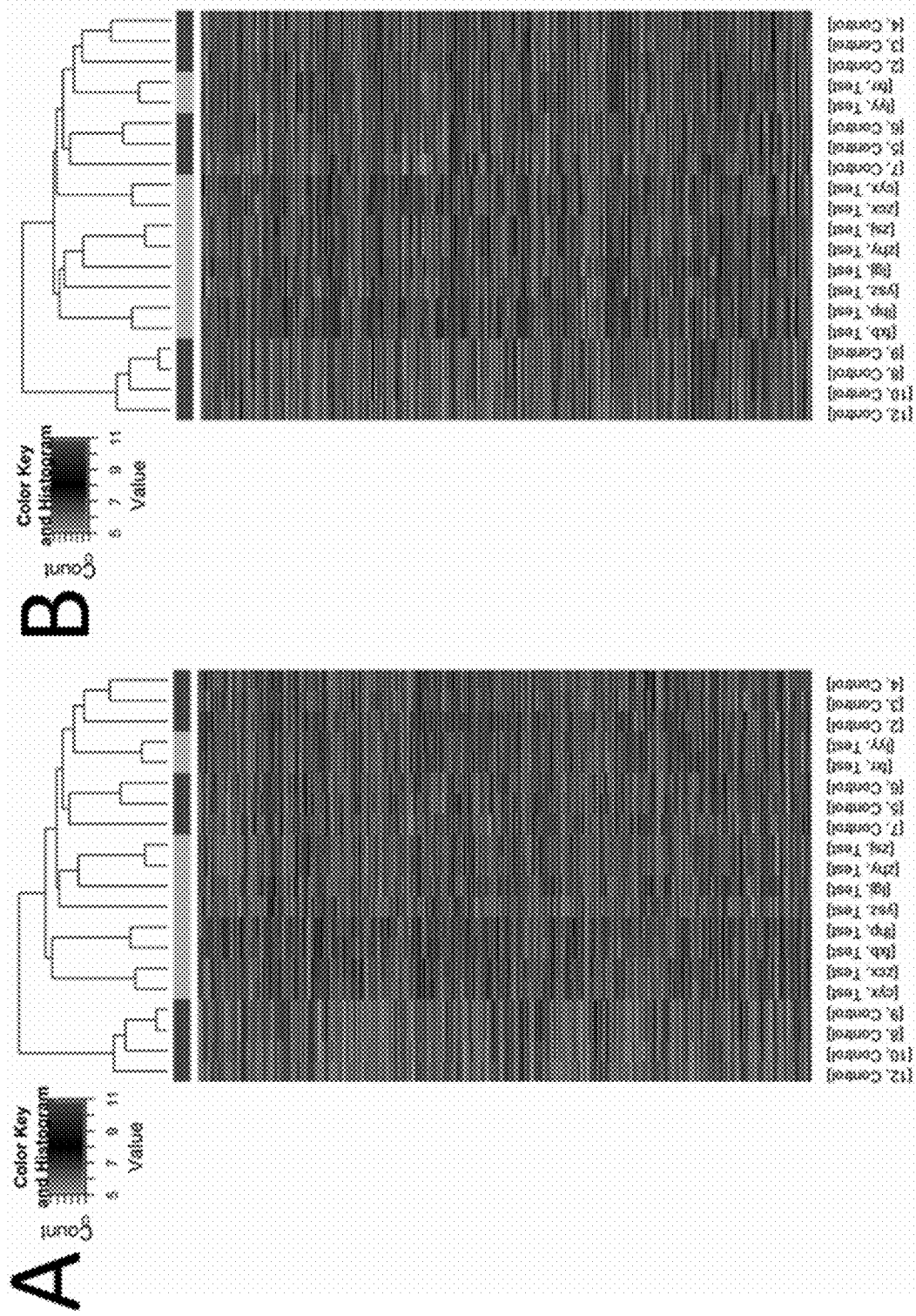
FIG. 1 shows the expression profiles of lncRNAs and mRNAs in aqueous humors of patients with glaucoma.

A of FIG. 1: Cluster analysis diagram of the expression profile of lncRNAs in aqueous humors of patients with glaucoma; B of FIG. 1: Cluster analysis diagram of the expression profile of mRNAs in aqueous humors of patients with glaucoma.

Figure 2:
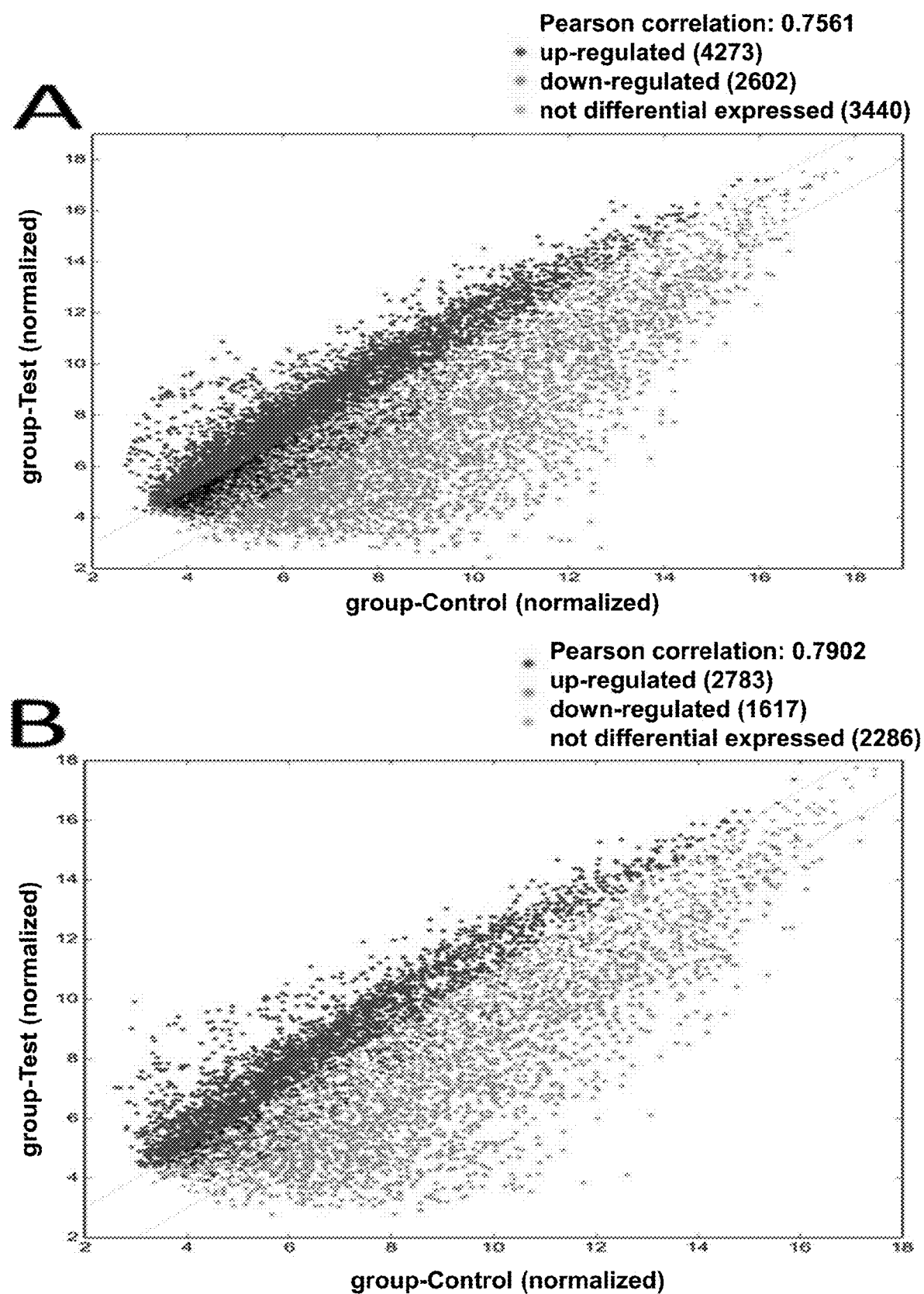

FIG. 2 shows differentially expressed lncRNAs and mRNAs in aqueous humors of patients with glaucoma;

A of FIG. 2: Compared with age-related cataracts, two-fold differentially expressed lncRNAs in aqueous humors of patients with glaucoma; B of FIG. 2: Compared with age-related cataracts, two-fold differentially expressed mRNAs in aqueous humors of patients with glaucoma.

Figure 3:
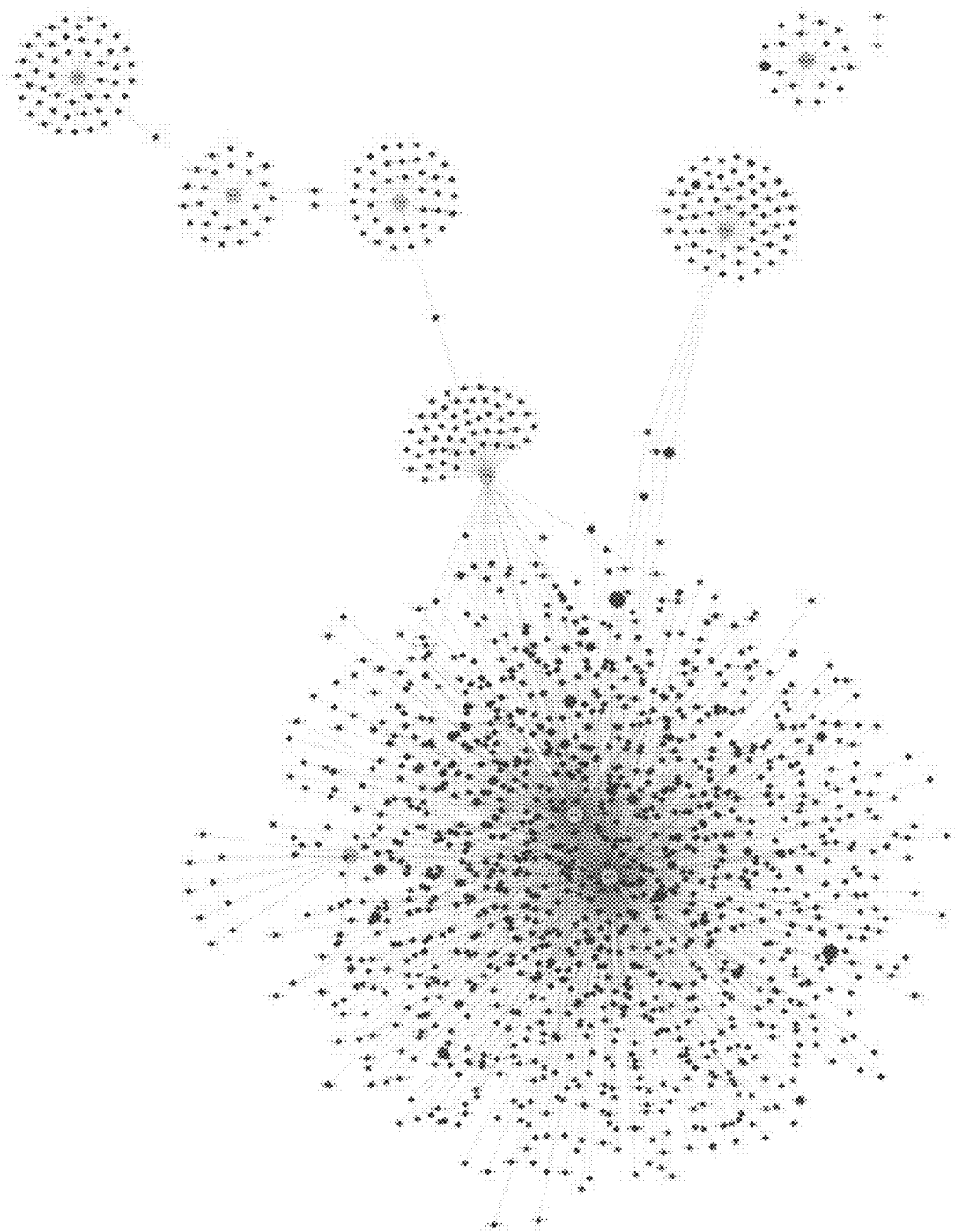

FIG. 3 shows CNC analysis diagrams of expressions of lncRNAs and mRNAs in aqueous humors of patients with glaucoma;

Red dots represent lncRNAs, blue dots represent mRNAs, solid lines represent a positive correlation, and dashed lines represent a negative correlation.

Figure 4:
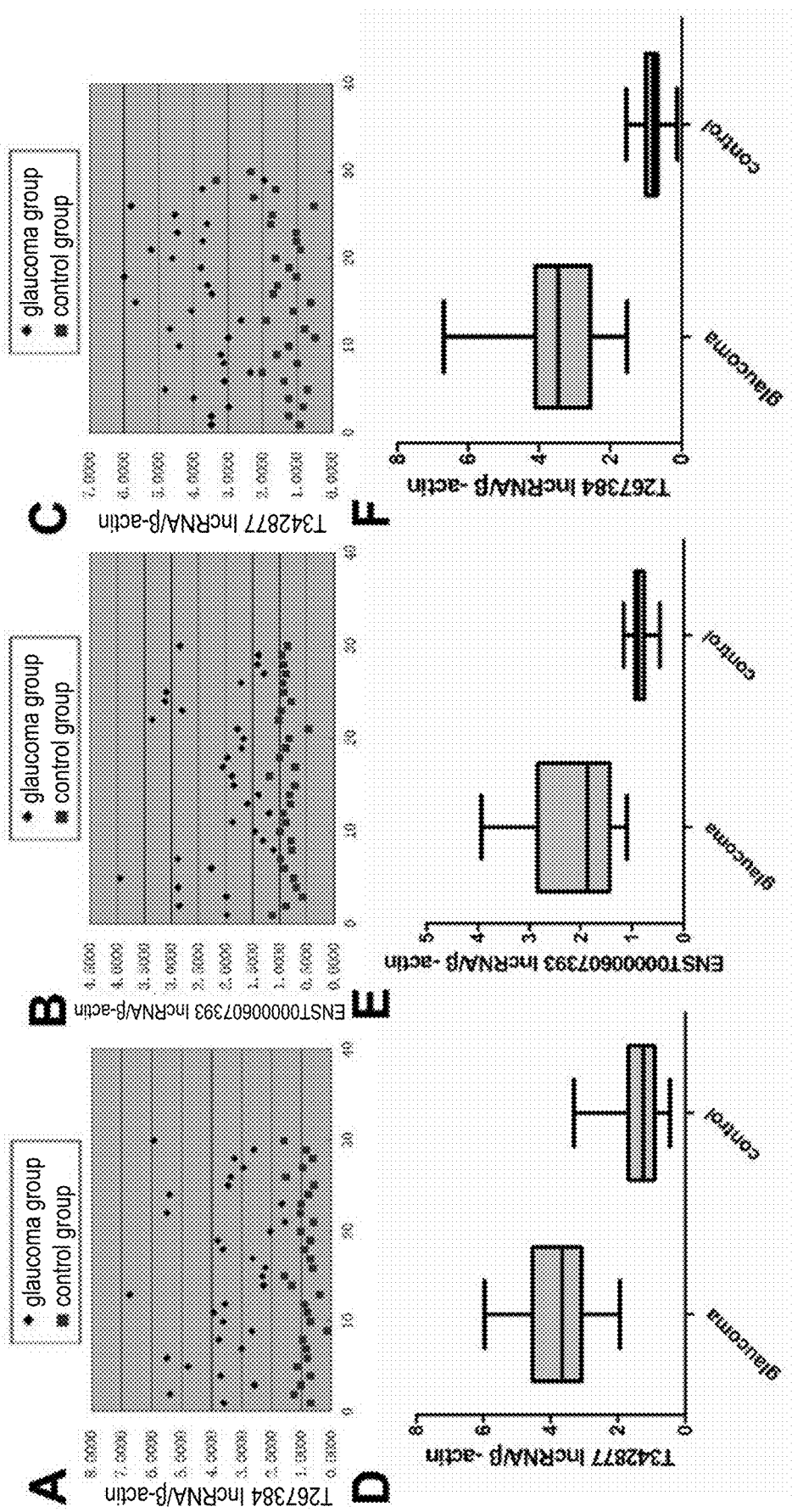

FIG. 4 shows the expression quantities of lncRNAs in aqueous humors of patients with glaucoma and age-related cataracts;

A-C of FIG. 4: scatter plots of expressions of T267384, ENST00000607393, and T342877 in aqueous humors of patients with glaucoma and age-related cataracts; D-F of FIG. 4: box plots of expression of T267384, ENST00000607393, and T342877 in aqueous humors of patients with glaucoma and age-related cataracts.

Figure 5:
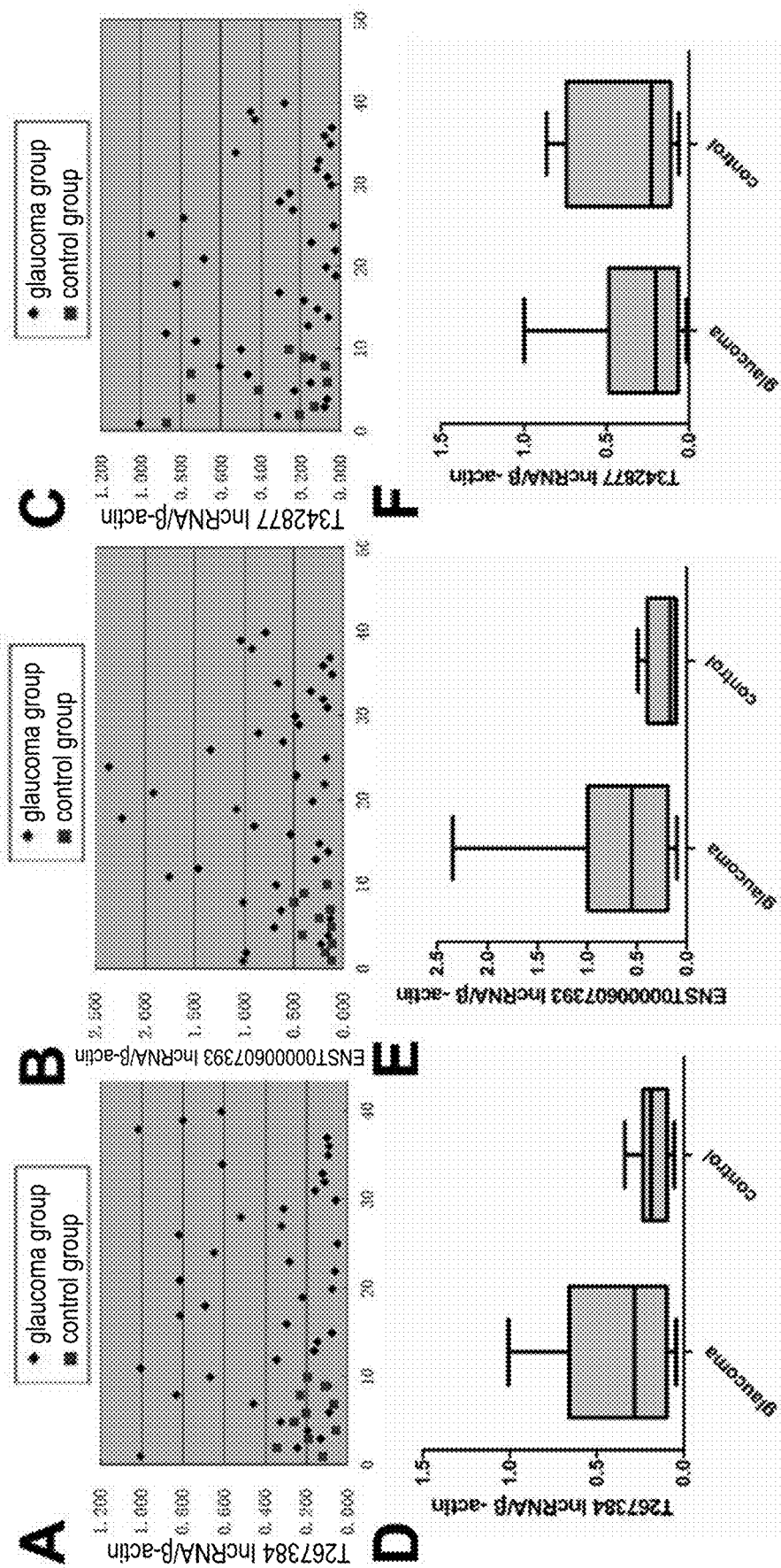

FIG. 5 shows the expression quantities of lncRNAs in iris tissues of patients with glaucoma and control people;

A-C of FIG. 5: scatter plots of expressions of T267384, ENST00000607393, and T342877 in iris tissues of patients with glaucoma and control people; D-F of FIG. 5: box plots of expressions of T267384, ENST00000607393, and T342877 in iris tissues of patients with glaucoma and control people.

Figure 6:
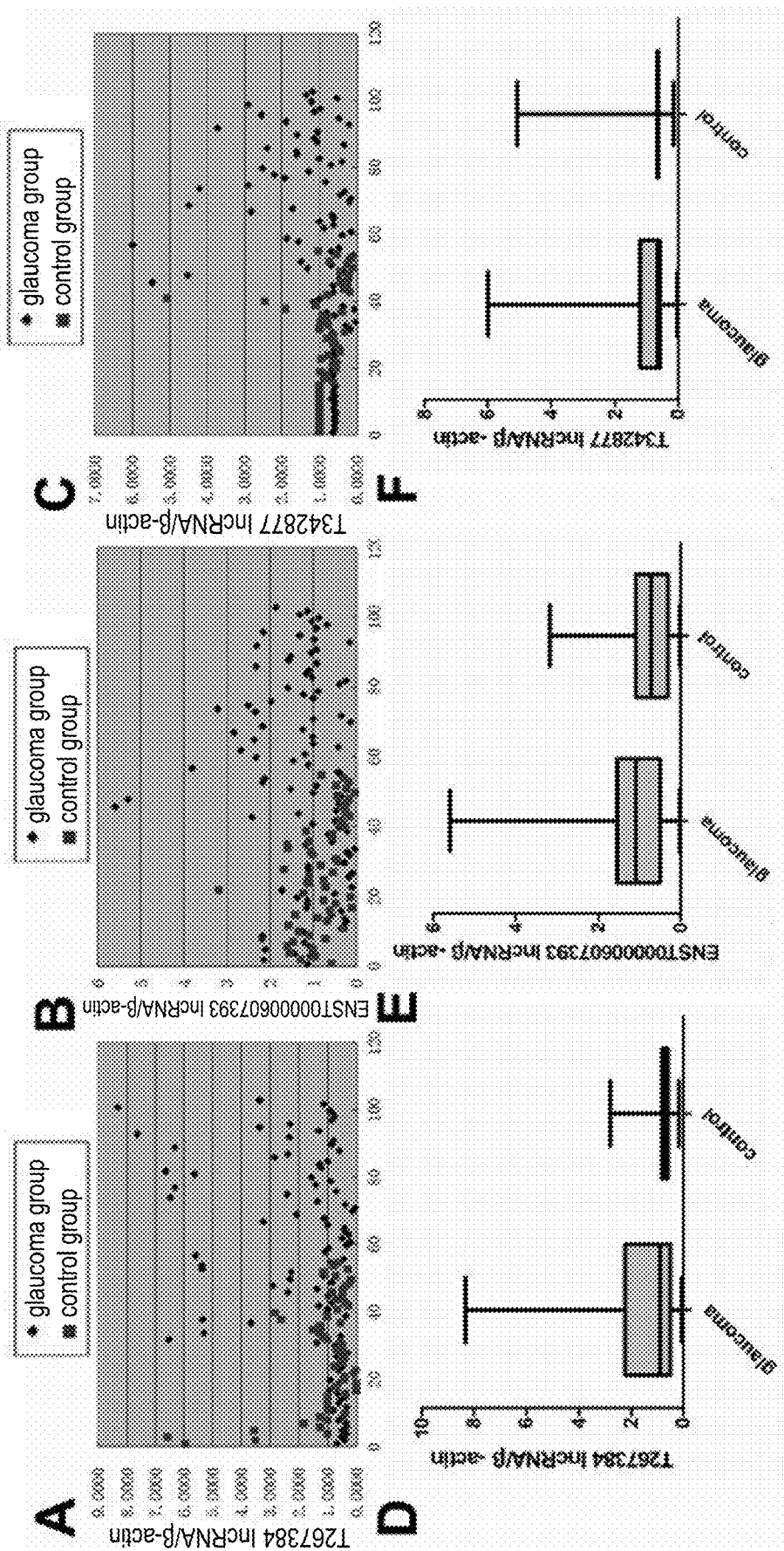

FIG. 6 shows the expression quantities of lncRNAs in serums of patients with glaucoma and control people;

A-C of FIG. 6: scatter plots of expressions of T267384, ENST00000607393, and T342877 in serums of patients with glaucoma and control people; D-F of FIG. 6: box plots of expressions of T267384, ENST00000607393, and T342877 in serums of patients with glaucoma and control people.

Figure 7:
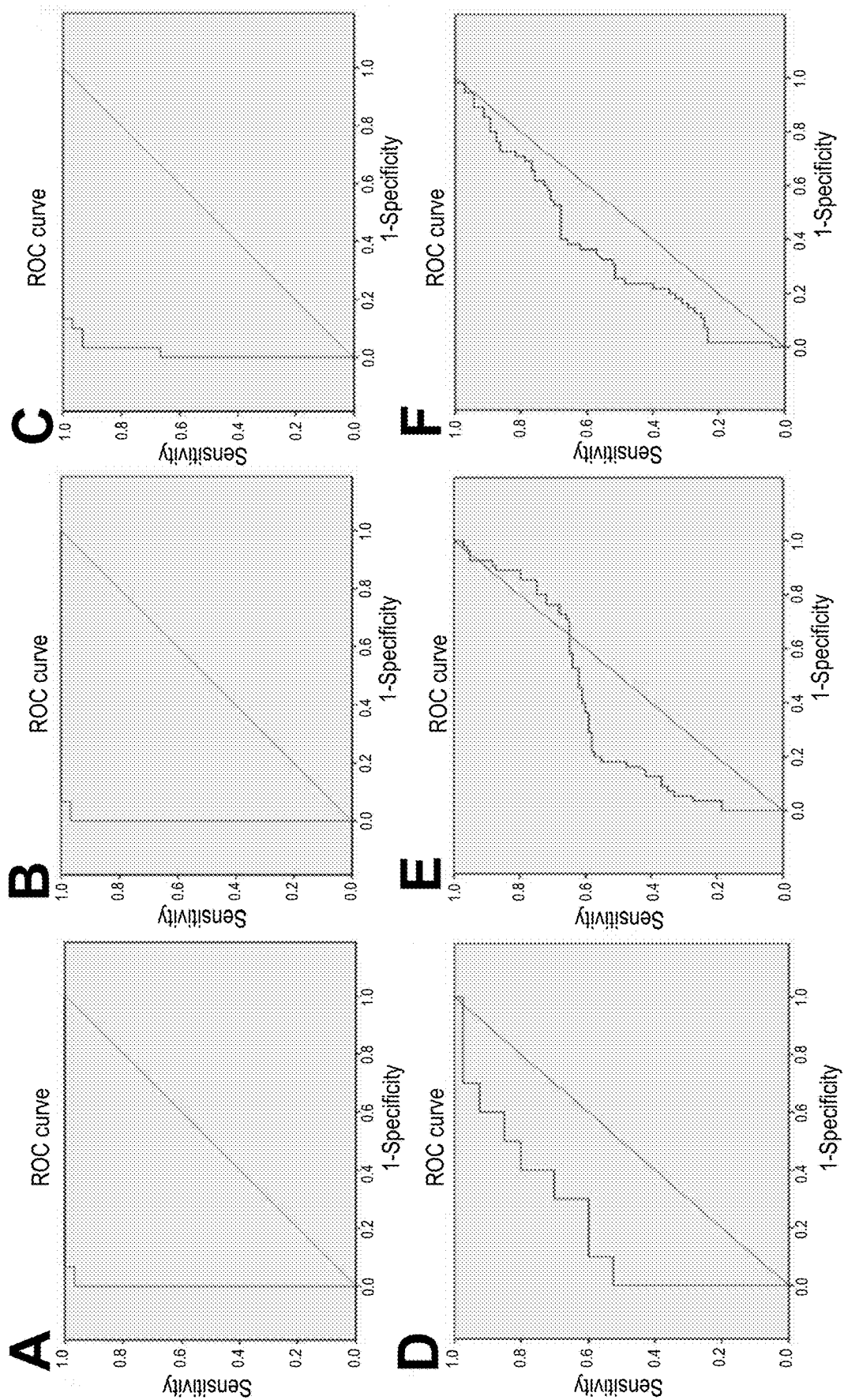

FIG. 7 shows ROC curves of lncRNAs for the diagnosis of glaucoma in different tissues;

A of FIG. 7: An ROC curve of using T267384 for the diagnosis of glaucoma in aqueous humor, with the area under the curve of 0.998; B of FIG. 7: An ROC curve of using ENST00000607393 for the diagnosis of glaucoma in aqueous humor, with the area under the curve of 0.998; C of FIG. 7: An ROC curve of using T342877 for the diagnosis of glaucoma in aqueous humor, with the area under the curve of 0.983; D of FIG. 7: An ROC curve of using ENST00000607393 for the diagnosis of glaucoma in the iris tissue, with the area under the curve of 0.793; E of FIG. 7: An ROC curve of using T267384 for the diagnosis of glaucoma in serum, with the area under the curve of 0.620; F of FIG. 7: An ROC curve of using ENST00000607393 for the diagnosis of glaucoma in serum, with the area under the curve of 0.638.

Figure 8:
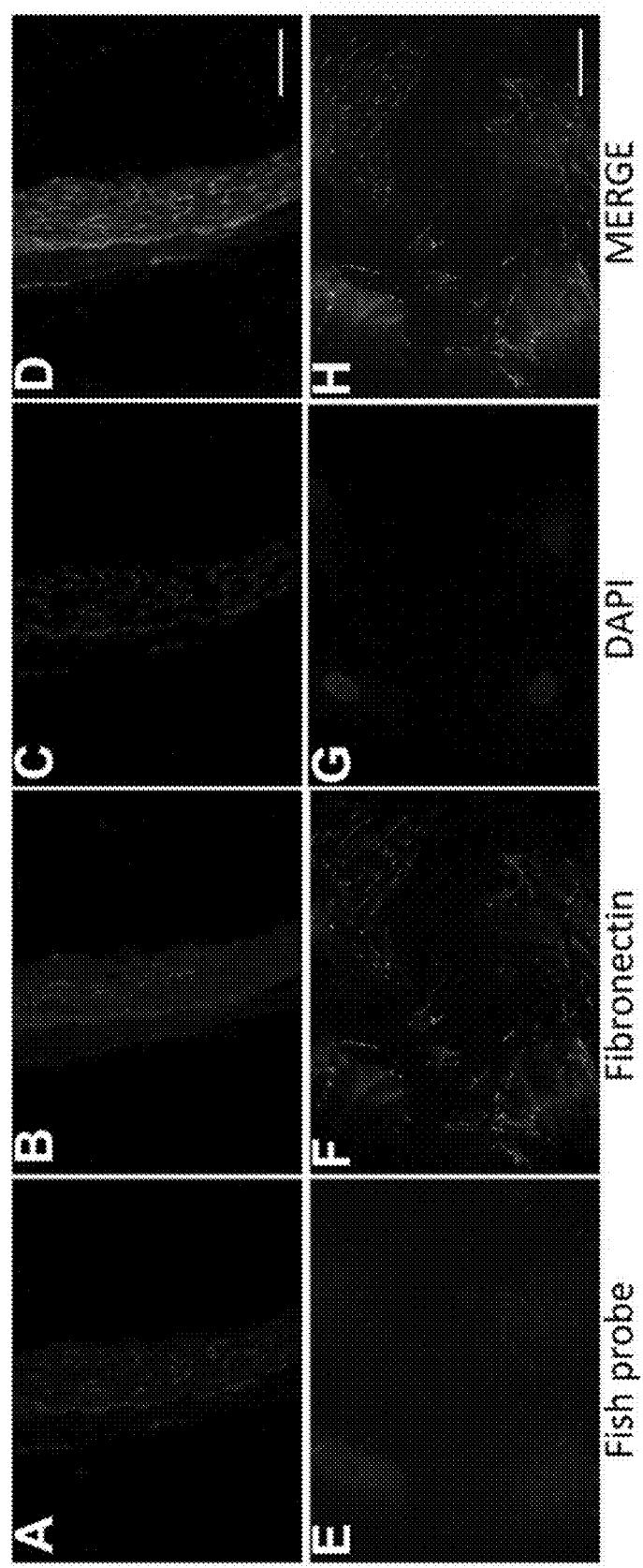

FIG. 8 shows the expressions of ENST00000607393 in trabecular meshwork cells of patients with glaucoma;

A-D of FIG. 8: it is found that ENST00000607393 is expressed in trabecular meshwork cells of patients with glaucoma by detecting with an ENST00000607393 specific FISH probe;

E-H of FIG. 8: it is found that ENST00000607393 is expressed in both the nuclei and cytoplasms of human primary trabecular meshwork cells by detecting with the ENST00000607393 specific FISH probe.

Figure 9:
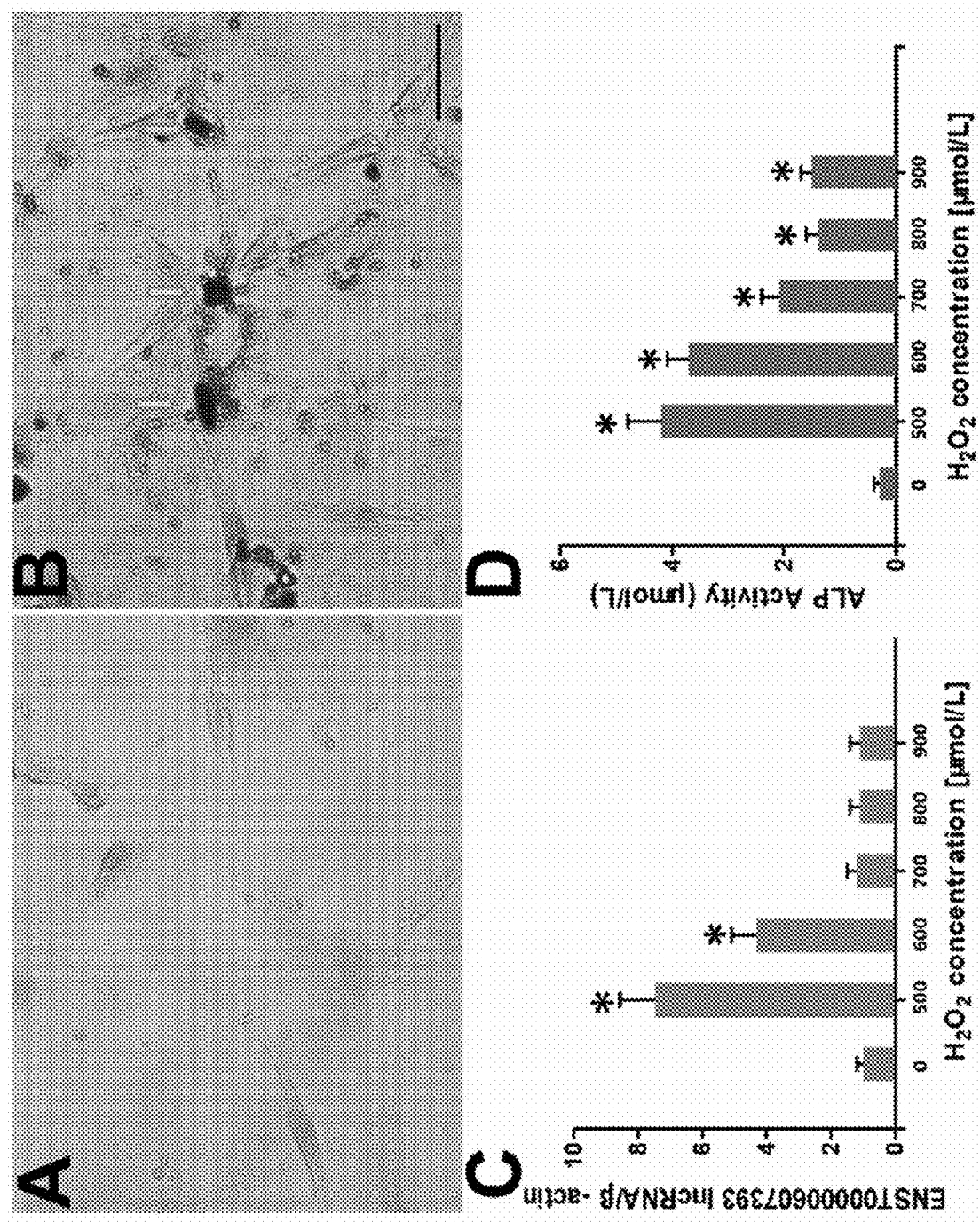

FIG. 9 shows the up-regulation of ENST00000607393 expression in human primary trabecular meshwork cells after hydrogen peroxide intervention;

A-B of FIG. 9: by staining with alizarin red, it is found that compared with a control group (A), calcium nodules appear in human primary trabecular meshwork cells after treating with a 500 µmol/L hydrogen peroxide solution for 48 h (B); C of FIG. 9 shows the expression level of ENST00000607393 in human primary trabecular meshwork cells after treating with different concentrations of hydrogen peroxide solutions for 48 h, in which * represents p<0.05; D of FIG. 9 shows the ALP activity in human primary trabecular meshwork cells after treating with different concentrations of hydrogen peroxide solutions for 48 h, in which * represents p<0.05.

Figure 10:
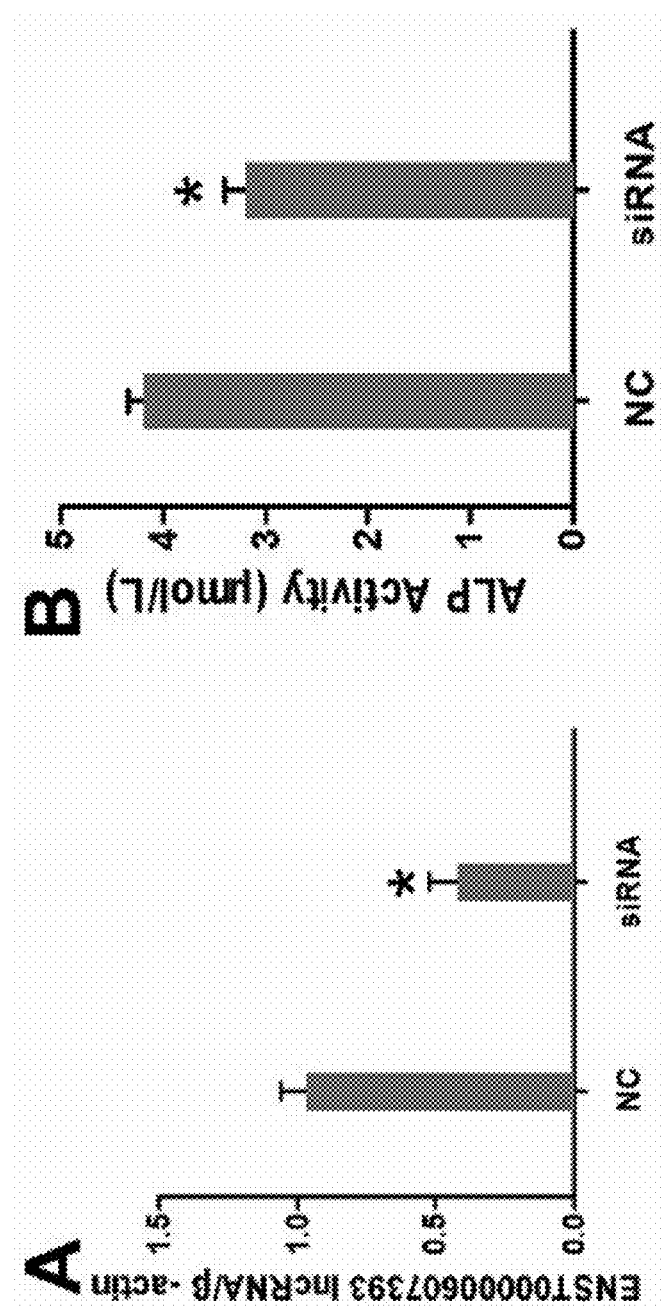

FIG. 10 shows that the down-regulation of ENST00000607393 expression can significantly decrease the calcification level of human primary trabecular meshwork cells; A of FIG. 10: the expression level of ENST00000607393 in human primary trabecular meshwork cells is down-regulated by an siRNA technology, and * represents p<0.05; B of FIG. 10: Compared with the control group, after the expression level of ENST00000607393 is down-regulated by siRNA, the ALP activity in human primary trabecular meshwork cells is significantly decreased, and * represents p<0.05.

DETAILED DESCRIPTION OF THE EMBODIMENTS

Embodiments of the Invention

The present invention is further illustrated in conjunction with the following embodiments but is not limited thereto.

Embodiment 1: Expression Profiles of lncRNAs and mRNAs in Aqueous Humors of Patients with Glaucoma 1.1 Materials and Reagents
1.1.1 Main Instruments
Common centrifuges and cryogenic centrifuges were purchased from Eppendorf Company; high-speed centrifuges were purchased from Beckman Company; Real-Time PCR instruments were purchased from ABI Company; pipettes and electric pipetting guns were purchased from Eppendorf Company; Q5000 was purchased from Quawell Technology Company; and ice machines were purchased from Sanyan Company.

1.1.2 Materials and Reagents

Different models of centrifuge tubes and PCR tubes were all purchased from Axygen Company; DEPC water was purchased from Dingguo Changsheng Company; Trizol was purchased from Invitrogen Company; TargetAmp™1-Round aRNA Amplification kits were purchased from epicentre Company; Transcriptor First Strand cDNA Synthesis kits were purchased from Roche Company; Quick Amp Labeling Kit, One-Color kits were purchased from Agilent Technologies Company; and human lncRNAs microarray chips were purchased from Arraystar Company.

1.1.3 Preparation of Reagents

Various reagents used for immunoblot were prepared according to the methods provided in *Molecular Cloning* (*Third Edition*).

1.2 Methods 1.2.1 Preparation of Aqueous Humor Samples

The research has been approved by the Ethics Committee of the Second Xiangya Hospital of Central South University. Informed consent was signed with all research subjects before surgery. Before the formal surgical procedure starts, 0.1 ml of an undiluted aqueous humor sample was taken from the limbus corneae with a 1 ml disposable sterile syringe, and immediately injected into an autoclaved 0.5 ml EP tube to be stored in a $-80°$ C. low temperature refrigerator in the dark for later use. All enrolled patients were patients with glaucoma and patients with age-related cataracts who needed surgery in our hospital. Inclusion criteria: 1. Primary open-angle glaucoma: having the following four items or having A, D, B or C: A. intraocular tension of more than 21 mmHg; B. glaucomatous optic disc damage and /RNFL defect; C. typical glaucomatous visual field defect; D. opened anterior chamber angle. 2. Normal tension glaucoma: having an optic disc change similar to POAG, RNFL and visual field damage, the intraocular tension being measured within 24 h to be all less than or equal to 21 mmHg, and opened anterior chamber angle. 3. Primary angle-closure glaucoma: having a glaucomatous optic disc change, RNFL and visual field damage, the intraocular tension of more than 21 mmHg, and narrowed or closed anterior chamber angle. 4. Age-related cataracts (control group): crystalline lenses having cortical and/or karyotype opacity and/or posterior capsule opacity. Exclusion criteria: 1. accompanied with systemic diseases such as hypertension and diabetes. 2. Secondary glaucoma. 3. Ophthalmic or neurological diseases that may affect vision, optic nerve, or color vision. 4. Reliability criteria for visual field detection: the fixation loss rate, false positive rate and/or false negative rate are more than 25%. 5. Age-related cataracts: complicated, traumatic, and congenital cataracts are excluded and those with other intraocular diseases are excluded, and hypermature cases are excluded.

1.2.2 RNA Extraction 0.1 ml of aqueous humor was taken and added with 0.5 ml of a Trizol reagent, and 0.1 ml of chloroform was added after shaking vigorously. Then, after centrifugation, precipitation and washing with 75% ethanol, the product was dissolved in 10 µl of DPEC water, and the RNA concentration of each tube was measured by a Q5000 instrument.

1.2.3 RNA Amplification

RNA was amplified by the TargetAmp™1-Round aRNA Amplification Kit 103 (epicentre) according to the steps as indicated in the manufacturer's instructions. The general steps are as follows: firstly, a single-stranded cDNA:RNA hybridization product was synthesized from an RNA sample, then the hybridization product was digested into small fragment sequences by an RNase H enzyme, and these small fragment sequences could assist in the synthesis of double-stranded cDNA. Finally, antisense RNA was synthesized by double-stranded cDNA transcription.

1.2.4 cDNA Synthesis and Labeling cDNA was synthesized by the Transcriptor First Strand cDNA Synthesis Kit (Roche) according to the steps as indicated in the manufacturer's instructions. The synthesized cDNA was labeled by the Quick Amp Labeling Kit, One-Color (Agilent Technologies).

1.2.5 Labeling Efficiency Quality Detection 1.5 µl of a labeled cDNA sample was taken, and the fluorescent labeling efficiency was detected by NanoDropND-1000.

1.2.6 Chip Hybridization

A labeled probe and the high-density chip (Human lncRNA microarray V4.0, Arraystar) were hybridized under standard conditions. A total of 40173 lncRNAs and 20730 mRNAs expression levels were detected by the chip.

1.2.7 Image Collection and Data Analysis

The fluorescence intensity of the chip was scanned by a GenePix 4000B chip scanner, and the experimental results were converted into digital data to be stored. P value <0.05 is considered that the difference is statistically significant.

1.3 Results 1.3.1 Expression Profiles of lncRNAs and mRNAs in Aqueous Humors of Patients with Glaucoma An average of $20653 \pm 569.9$ lncRNAs and $11265 \pm 268.3$ mRNAs were detected in ten aqueous humor samples of patients with glaucoma. Among them, the number of lncRNAs that were detected in all the ten aqueous humor samples of patients with glaucoma was 11728, and the number of mRNAs that were detected in all the ten aqueous humor samples of patients with glaucoma was 6686.

1.3.2 Differentially Expressed lncRNAs and mRNAs in Aqueous Humors of Patients with Glaucoma Compared with age-related cataracts, the number of lncRNAs of which the expression was up-regulated by two folds in the aqueous humors of patients with glaucoma was 4372, and the number of lncRNAs of which the expression was down-regulated by two folds was 2602. Compared with age-related cataracts, the number of mRNAs of which the expression was up-regulated by two folds in the aqueous humors of patients with glaucoma was 2783, and the number of mRNAs of which the expression was down-regulated by two folds was 1617.

1.4 Results

Because of its ease taking, individual specificity and relatively little impact from other organs of the body, the aqueous humor is a valuable research object for biomarker-related research of eye diseases. Moreover, although many researches on glaucoma-related epidemiological and genetic risk factors have been reported, there are relatively few related researches on aqueous humor as a research object. Therefore, we believe that the aqueous humor has the potential to be applied to the genetics research related to glaucoma in the future. The human aqueous humor sample is small in size due to sampling limitations. To overcome the problem, an RNA amplification step was added before chip hybridization, so as to ensure the smooth progress of the subsequent steps. By using the lncRNAs chip microarray analysis method, 11728 lncRNAs and 6686 mRNAs were detected in ten glaucoma aqueous humor samples, which were significantly different from the expression profiles of lncRNAs and mRNAs in the aqueous humors of patients with age-related cataracts. Therefore, the expression profiles of lncRNAs and mRNAs in the aqueous humors exhibit individual specificity and disease specificity. As far as we know, this is the first research on the expression profiles of lncRNAs and mRNAs related to glaucoma aqueous humors.

Embodiment 2: Confirming of Correlation Between Specific lncRNAs and mRNAs in Aqueous Humor by CNC Analysis To further investigate the possible functions of lncRNAs expressed in aqueous humors of patients with glaucoma, lncRNAs with a significant correlation with mRNAs expression of glaucoma-related genes were confirmed by CNC (coding-noncoding gene co-expression) analysis. CNS analysis is an analytical method that links lncRNA to mRNA by co-expression data of lncRNA and mRNA. Through CNC analysis, mRNA with the same expression pattern as a certain lncRNA can be found. Through the functions of these mRNAs, lncRNA can be linked to specific signaling pathways or disease states, thereby conveniently predicting the functions of lncRNA and revealing its mechanism of action.

2.1 Methods

The mRNAs that were differentially expressed in the aqueous humor and had a correlation with the occurrence and development of glaucoma were selected, and the expression data of these mRNAs in the aqueous humors of different patients with glaucoma were averaged; the Pearson correlation coefficient (PCC) and the false discovery rate (FDR) between the data after standardization of selected mRNAs and the differentially expressed lncRNAs related data in the aqueous humors of patients with glaucoma were solved; records with PCC ≥0.90 and FDR ≤0.05 were selected; and drawing was carried out by a Cytoscape 2.8.3 tool using related records.

2.2 Results

Compared with age-related cataracts, there were the following ten mRNAs that are differentially expressed in the aqueous humors of patients with glaucoma and have the correlation with the occurrence and development of glaucoma: bone morphogenetic protein 2 (BMP2), ependymin related gene 1 (EPDR1), transforming growth factor beta 1 (TGFB1), forkhead box protein E3 (FOXE3), growth hormone secretagogue receptor (GHSR), forkhead box protein C1 (FOXC1), transmembrane and coiled-coil domains 1 (TMCO1), pleckstrin homology domain containing A7 (PLEKHA7), optineurin (OPTN) and integrin subunit beta 5 (ITGB5). In the aqueous humors of patients with glaucoma, there were ten lncRNAs with the Pearson correlation coefficient greater than 0.9 and the false discovery rate of less than 0.05 related to the expression of these mRNAs.

In the obtained results, BMP2 has the most types of related lncRNAs, which means that many lncRNAs may have a similar biological background to the gene. BMP2 belongs to the transforming growth factor-β (TGF-β) superfamily protein. It has a strong ability to promote osteogenesis and induce pluripotent mesenchymal stem cells to differentiate into an osteoblast cell line. Similarly, BMP2 can cause osteoblast-like cell characteristics in human primary trabecular meshwork cells in vitro. In in-vivo experiments, BMP2 was overexpressed by adenovirus transfection, which further proves that the up-regulation of the expression level of a BMP2 gene at a trabecular meshwork part can cause a significant increase in intraocular tension in a rat under the condition of without affecting the basic structure of the part. Further research proves that a mouse of which the BMP2 gene at the trabecular meshwork part is overexpressed can be used as one of the animal models for glaucoma related research. Therefore, the gene is closely related to the occurrence and development of glaucoma, which further indicates that the expression profiles of lncRNAs and mRNAs in aqueous humors of patients with glaucoma show high disease specificity.

Embodiment 3

In the ten lncRNAs in Embodiment 2 verified in the aqueous humors of patients with glaucoma and age-related cataracts by qRT-PCR, the differential expression quantities of seven lncRNAs in the two types of aqueous humors have statistical difference, and the differential expression quantities of three lncRNAs in the two types of aqueous humors have no statistical difference. Then T267384, ENST00000607393 and T342877 with the most significant differential expression quantities were selected for further verification.

Embodiment 4

A qRT-PCR detection method was used to verify the expression levels of three lncRNA molecules with the most significant difference in Embodiment 3 in aqueous humors, iris tissues and serums, and analyze the difference of expression quantities between patients with glaucoma and the normal people.

4.1 Materials and Reagents 4.1.1 Main Instruments

Common centrifuges and cryogenic centrifuges were purchased from Eppendorf Company; high-speed centrifuges were purchased from Beckman Company; Real-Time PCR instruments were purchased from ABI Company; pipettes and electric pipetting guns were purchased from Eppendorf Company; Q5000 was purchased from Quawell Technology Company; and ice machines were purchased from Sanyan Company.

4.1.2 Materials and Reagents

Different models of centrifuge tubes and PCR tubes were all purchased from Axygen Company; DEPC water was purchased from Dingguo Changsheng Company; Trizol was purchased from Invitrogen Company; and reverse transcription kits and fluorescent quantitative kits were all purchased from Roche Company.

4.1.3 Preparation of Reagents

Various reagents used for immunoblot were prepared according to the methods provided in *Molecular Cloning* (*Third Edition*).

4.2 Methods 4.2.1 Preparation of Aqueous Humor, Serum and Iris Samples

The aqueous humor samples were prepared as described in the step 1.2.1. The serum samples were taken from patients with glaucoma and people from the healthy control group. The inclusion and exclusion criteria for patients with glaucoma were the same as those described in 1.2.1. The serum from the control group was taken from healthy people matched with patients in the glaucoma group in age and gender. The iris sample was taken from the glaucoma patient group and the control group. The inclusion and exclusion criteria for patients with glaucoma were the same as those described in 1.2.1. The iris sample from the control group was taken from the iris tissues of cornea donors of the Xiangya Second Hospital, which are matched with the patients with glaucoma in age and gender.

4.2.2 RNA Extraction 0.1 ml of aqueous humor or iris tissue was added with 0.5 ml of a Trizol reagent, and 0.1 ml of chloroform was added after shaking vigorously. Then, after centrifugation, precipitation and washing with 75% ethanol, the product was dissolved in 20 μl of DPEC water, and the RNA concentration of each well was measured by a Q5000 instrument. Peripheral venous blood was allowed to stand for 30 minutes, and placed in a centrifuge to be centrifuged at 3200 rpm for 10 minutes, a supernatant serum was taken by a sterile pipette, and RNA was extracted by the same step as above.

4.2.3 qRT-PCR

According to the manufacturer's instructions, RNA was reversely transcribed into cDNA by a reverse transcription enzyme firstly, and then the cDNA was amplified by a PCR method, and the quantity of the quantitatively amplified product was detected in real time by measuring a fluorescence intensity signal.

4.2.4 Data Analysis

Data was processed by SPSS19.0 version statistical software. Measurement data was expressed as median±quartile spacing, and glaucoma/cataract represented the median ratio of the two groups and Mann-whitney U test was performed by comparison. P value <0.05 was considered that the difference was statistically significant.

4.3 Results

To further expand the aqueous humor sample size to verify the expression levels of the related lncRNAs and to explore the expression quantities of specific lncRNAs in the serums and irises of patients with glaucoma, qRT-PCR was used to detect the expression levels of T267384, ENST00000607393 and T342877 in 60 aqueous humor samples (30 aqueous humor samples of patients with glaucoma, and 30 aqueous humor samples of age- and gender-matched patients with age-related cataracts), 50 iris tissues (40 iris tissue samples of patients with glaucoma, and 10 iris tissues of age- and gender-matched cornea donors) and 158 serum samples (103 serum samples of patients with glaucoma, and 55 serum samples of age- and gender-matched healthy people). The results show that the expression quantities of three lncRNAs have statistical difference in the two types of aqueous humor samples, and the expression quantities thereof in the aqueous humors of patients with glaucoma are 4.4036, 2.1467 and 2.9692 times larger than those in the aqueous humors of patients with age-related cataracts; the expression quantities of ENST00000607393 in the two types of iris tissues have statistical difference, the expression quantity thereof in the iris tissues of patients with glaucoma is 3.3436 times larger than that in the iris tissues from the control group, while the expression quantities of T267384 and T342877 have no statistical difference; the expression quantities of T267384 and ENST00000607393 have statistical difference in the two serum samples, and the expression quantities thereof in the serums of patients with glaucoma were 1.2878 and 1.5301 times larger than those in the serums from the control group, while the expression quantity of T342877 has no statistical difference. (Tables 1, 2, and 3) (FIGS. 4, 5, and 6). To further understand the effectiveness of these three lncRNAs in the diagnosis of glaucoma in different tissues, the receiver operating characteristic (ROC) curves (FIG. 7) were drawn by using the obtained data. It is found that the areas under the ROC curves of T267384, ENST00000607393 and T342877 for the diagnosis of glaucoma in the aqueous humor samples are 0.998, 0.998 and 0.983, respectively; the area under the ROC curve of ENST00000607393 for the diagnosis of glaucoma in iris tissue is 0.793; the areas under the ROC curves of T267384 and ENST00000607393 for the diagnosis of glaucoma in serum samples are 0.620 and 0.638, respectively. When the diagnostic values of T267384, ENST00000607393, and T342877 in the aqueous humors are set to 1.5437, 1.1485, and 2.1052, the sensitivity/specificity of diagnosis is 0.967/0.967, 0.967/0.967, and 0.967/0.900, sequentially; when the diagnostic value of ENST00000607393 in the iris tissues is set to 0.2470, the sensitivity/specificity of diagnosis is 0.700/0.700; when the diagnostic values of T267384 and ENST00000607393 in serums are set to 0.7191 and 0.8376, the sensitivity/specificity of diagnosis is 0.612/0.600 and 0.680/0.600.

TABLE 1

Expression Quantities of Three lncRNAs in Aqueous Humors

| lncRNAs | Glaucoma group | Cataract group | Glaucoma/cataract | P value |
| --- | --- | --- | --- | --- |
| T267384 | 3.4793 ± 1.2848 | 0.7901 ± 0.3129 | 4.4036 | 0.000 |
| ENST00000607393 | 1.8700 ± 1.3398 | 0.8711 ± 0.1666 | 2.1467 | 0.000 |
| T342877 | 3.6545 ± 1.4040 | 1.2308 ± 0.7356 | 2.9692 | 0.000 |

TABLE 2

Expression Quantities of Three lncRNAs in Iris Tissues

| lncRNAs | Glaucoma group | Control group | Glaucoma/cataract | P value |
| --- | --- | --- | --- | --- |
| T267384 | 0.2835 ± 0.5452 | 0.1875 ± 0.1097 | 1.5120 | 0.121 |
| ENST00000607393 | 0.5537 ± 0.7749 | 0.1656 ± 0.2401 | 3.3436 | 0.005 |
| T342877 | 0.2028 ± 0.3966 | 0.2269 ± 0.5187 | 0.8938 | 0.482 |

TABLE 3

Expression Quantities of Three lncRNAs in Serums

| lncRNAs | Glaucoma group | Control group | Glaucoma/cataract | P value |
| --- | --- | --- | --- | --- |
| T267384 | 0.8944 ± 1.6348 | 0.6945 ± 0.1908 | 1.2878 | 0.013 |
| ENST00000607393 | 1.0905 ± 1.0336 | 0.7127 ± 0.7648 | 1.5301 | 0.004 |
| T342877 | 0.6520 ± 0.6056 | 0.6503 ± 0.0527 | 1.0026 | 0.280 |

TABLE 4

Sensitivity and Specificity of Diagnosis of Three lncRNAs in Different Tissues

| Cut-off values | Sensitivity | Specificity |
| --- | --- | --- |
| 1.5437 (T267384 aqueous humor) | 0.967 | 0.967 |
| 1.1485 (ENST00000607393 aqueous humor) | 0.967 | 0.967 |
| 2.1052 (T342877 aqueous humor) | 0.967 | 0.900 |
| 0.2470 (ENST00000607393 iris) | 0.700 | 0.700 |
| 0.7191 (T267384 serum) | 0.612 | 0.600 |
| 0.8376 (ENST00000607393 serum) | 0.680 | 0.600 |

Embodiment 5

Trabecular meshwork cells and Schlemm's tubes were important components of an aqueous humor outflow channel. Calcification of trabecular meshwork cells was one of the possible pathological changes in the occurrence and development of glaucoma. From CNC analysis, it could be seen that ENST00000607393 was positively correlated with the expression level of BMP2, and BMP2 was a gene closely related to the calcification of trabecular meshwork cells and mRNA expression level of BMP2 was up-regulated in aqueous humors of patients with glaucoma. Therefore, in order to further understand the relationship between ENST00000607393 and the calcification of trabecular meshwork cells, subsequent research will be performed by RNA in situ hybridization, siRNA interference and other means by using human primary trabecular meshwork cells as a research object.

5.1 Materials and Reagents 5.1.1 Main Instruments

Cell incubators were purchased from Forma Company; Nanodrop spectrophotometers were purchased from Thermo Scientific Company; common centrifuges and cryogenic centrifuges were purchased from Eppendorf Company; Real-Time PCR instruments were purchased from ABI Company; pipettes and electric pipetting guns were purchased from Eppendorf Company; a microplate reader was purchased from PerkinElmer Company; freezing microtomes were purchased from Thermo Scientific Company; Q5000 was purchased from Quawell Technology Company; ice machines were purchased from Sanyan Company; and fluorescence microscopes were purchased from Olympus Company.

5.1.2 Materials and Reagents

Different models of cell culture flasks, culture dishes and pipettes were all purchased from BD Bioscience Company; different models of centrifuge tubes and PCR tubes were all purchased from Axygen Company; Trizol was purchased from Invitrogen Company; cell mediums, fetal bovine serums and double-antibodies were purchased from Gibco Company; Lipofectamine 3000 was purchased from Invitrogen Company; specific FISH probes were purchased from Shanghai Jima Company; Alkaline Phosphatase Assay Kit and ALP enzyme were purchased from Abcam Company; hydrogen peroxide solutions and alizarin red were purchased from Sigma Company; and the remaining common biochemical reagents were all purchased from Sigma Company or companies providing an analytical pure grade.

5.1.3 Preparation of Reagents

Various reagents used for immunoblot were prepared according to the methods provided in *Molecular Cloning (Third Edition)*.

5.2 Methods 5.2.1 Isolation and Culture of Human Primary Trabecular Meshwork Cells Human primary trabecular meshwork cells were isolated from the trabecular meshworks of cornea donors from the Xiangya Second Hospital. The trabecular meshworks were torn off in strips under a microscope and cut into small pieces. After adhering for 30 minutes, an RPMI-1640 medium (containing 10% of fetal bovine serum and 1% of penicillin-streptomycin) was added and placed in a 37° C. incubator containing 5% of carbon dioxide to be cultured. After the cells began to grow, the medium was changed once every 3 days. Passage was carried out by digesting with 0.25% trypsin. The human primary trabecular meshwork cells were taken to prepare a cell stretched preparation, and immunofluorescence staining was performed on fibronectin and α-smooth muscle actin (α-SMA) to identify the trabecular meshwork cells. The human primary trabecular meshwork cells used in subsequent experiments were cultured in a Dulbecco's Modified Eagle's Medium (DMEM), 10% of fetal bovine serum and 1% of penicillin-streptomycin. 4 to 6 generations of human primary trabecular meshwork cells were used in the experiments.

5.2.2 Fluorescence In Situ Hybridization (FISH) Probe Localization

The sequences of three FISH probes were 5'-AGAAGGCTCGGCGTAGGGA-3' (SEQ ID NO: 6), 5'-TGATAATGAGAAGGCTCGGCGTA-3' (SEQ ID NO: 7), and 5'-GAGCCCGAGTTCGCTGGAAT-3'(SEQ ID NO: 8), respectively.

The FISH probe was diluted to a stock solution having a concentration of 20 uM by using double distilled pure water for later use. The human primary trabecular meshwork cells were inoculated in a 6-well plate at $1 \times 10^5$, and the medium was sucked out after 24 hours, and the cells were ready for use. After the cells were treated with absolute ethanol, 0.1% triton X-100, and 2×SSC water, 100 μl of a probe liquid mixture was added to each well and placed in a 37° incubator overnight. On the next day of hybridization, 100 μl of a DAPI staining solution was added after treating with 0.4×SSC and 2×SSC to stain for 20 minutes in the dark, and then observed under a fluorescence microscope. The trabecular meshworks of patients with glaucoma were embedded with an OCT compound and then frozen and sectioned. After fixation with 4% formaldehyde, permeabilization and washing, FISH probe hybridization was carried out by the same steps as above.

5.2.3 Hydrogen Peroxide Intervention

ALP activity, namely, alkaline phosphatase activity, was one of markers of cell calcification. Therefore, the ALP activity in trabecular meshwork cells could reflect the calcification level of the cells. Because the ALP activity in normal cells (when the hydrogen peroxide intervention was not used) was very low, the use of hydrogen peroxide intervention aims to establish an in vitro cell research model.

The human primary trabecular meshwork cells were inoculated in the 6-well plate at $1\times10^5$, and a 30% hydrogen peroxide solution was diluted to 500, 600, 700, 800, and 900 μmol/L with cell media, respectively. 2 ml of the above concentration of hydrogen peroxide solution was added to the 6-well plate, and after 48 hours, the medium was sucked out for subsequent experiments.

5.2.4 Alizarin Red Staining

The human primary trabecular meshwork cells were taken to prepare the cell stretched preparation. After the above control group and the cells treated with different concentrations of hydrogen peroxide solutions were treated with 4% paraformaldehyde and PBS, 1 ml of 0.1% alizarin red-Tris-HCl was added to each well, placed in a 37° incubator for 30 minutes and then observed under an optical microscope.

5.2.5 Alkaline Phosphatase (ALP) Activity Detection

The human primary trabecular meshwork cells were inoculated in the 6-well plate at $1\times10^5$, the above control group and the cells treated with different concentrations of hydrogen peroxide solutions were treated according to the manufacturer's instructions and the numerical values were read on a microplate reader under OD405 nm.

5.2.6 siRNA Interference

A negative control has a positive-sense strand sequence of 5'-UUCUCCGAACGUGUCACGU-3' (SEQ ID NO: 4) and an antisense strand sequence of 5'-ACGUGACACGUUCG-GAGAA-3' (SEQ ID NO: 5). The siRNA against ENST00000607393 has a positive-sense strand sequence of 5'-GCAGGCGUGUGCAUUUCUU-3' (SEQ ID NO: 2) and an antisense strand sequence of 5'-AAGAAAUGCACACGCCUGC-3' (SEQ ID NO: 3). One day before transfection, the cells were inoculated in the 6-well plate at $1\times10^5$. 30 μmol siRNA was added to 50 μl of a serum-free DMEM medium, and gently mixed well, 6 μl of a lipofectamin reagent was diluted with 50 μl of the serum-free DMEM medium, the diluted siRNA and the lipofectamin reagent were mixed well and placed for 5 minutes at room temperature. An siRNA/lipofectamin compound was then added to the cell medium to be cultured for 48 hours in the 37° incubator containing 5% of carbon dioxide for subsequent experiments.

5.2.7 RNA Extraction

After the human primary trabecular meshwork cells were inoculated in the 6-well plate at $1\times10^5$ and subjected to different treatments, the medium was sucked out and washed with PBS for three times, 0.5 ml of the Trizol reagent was added, and 0.1 ml of chloroform was added after shaking vigorously. Then, after centrifugation, precipitation and washing with 75% ethanol, the product was dissolved in 20 μl of DPEC water, and the RNA concentration of each well was measured by a Q5000 instrument.

5.2.8 qRT-PCR

According to the manufacturer's instructions, RNA was reversely transcribed into cDNA by a reverse transcription enzyme firstly, then the cDNA was amplified by a PCR method, and the quantity of the quantitatively amplified product was detected in real time by measuring a fluorescence intensity signal.

5.3 Results 5.3.1

ENST00000607393 was expressed in the trabecular meshworks and the nuclei and cytoplasms of the human primary trabecular meshwork cells of patients with glaucoma.

To observe the expression situation of ENST00000607393 in the trabecular meshworks of patients with glaucoma, after the trabecular meshworks of patients with glaucoma were frozen and sectioned, the immunofluorescence staining of ENST00000607393 specific FISH probes and a trabecular meshwork cell marker Fibronectin were simultaneously performed. It was observed that ENST00000607393 was expressed in the trabecular meshwork cells of trabecular meshworks of patients with glaucoma (FIG. 8, A-D). To further determine the sublocalization of ENST00000607393 in the trabecular meshwork cells, the immunofluorescence staining of ENST00000607393 specific FISH probes and the trabecular meshwork cell marker Fibronectin were simultaneously performed. It was further observed that ENST00000607393 was expressed in the nuclei and cytoplasms of the human primary trabecular meshwork cells (FIG. 8, E-H).

5.3.2 Increased Calcification Level of Human Primary Trabecular Meshwork Cells after Hydrogen Peroxide Intervention After the human primary trabecular meshwork cells were treated with 0, 500, 600, 700, 800 and 900 μmol/L hydrogen peroxide solutions for 48 hours respectively, the expression level of ENST00000607393, alizarin red staining and ALP activity were determined. The results show that compared with the control group, after intervening by the 500 and 600 μmol/L hydrogen peroxide solutions for 48 hours respectively, the expression level of ENST00000607393 in human primary trabecular meshworks was significantly increased, and the increase ratio was 7.21 and 4.36, respectively, and after intervening by the 700, 800 and 900 μmol/L hydrogen peroxide solutions for 48 hours respectively, there was no significant change in the expression level of ENST00000607393 in the cells (FIG. 9, C). By staining with alizarin red, it was observed that compared with the control group, after intervening by the 500 μmol/L hydrogen peroxide solution for 48 hours, calcium nodules were formed in the human primary trabecular meshwork cells (FIG. 9, A-B). Compared with the control group, after intervening by 500, 600, 700, 800 and 900 μmol/L hydrogen peroxide solutions for 48 hours respectively, the ALP activity in the cells were all increased significantly to different degrees.

5.3.3 Significant Decreased Calcification Level of Human Primary Trabecular Meshwork Cells by Down-Regulation of ENST00000607393 Expression To clarify the correlation between the expression level of ENST00000607393 and the calcification of human primary trabecular meshwork cells, the expression level of ENST00000607393 in human primary trabecular meshwork cells was firstly down-regulated to 46.21% of the control group by siRNA interference. Under the condition that the cells were intervened by the 500 μmol/L hydrogen peroxide solution for 48 hours, it was observed that the down-regulation of ENST00000607393 expression can significantly decrease the ALP activity in the human primary trabecular meshwork cells compared with the control group.

Pathological calcification of trabecular meshwork cells is one of the important pathological characteristics of glaucoma. Research proves that the trabecular meshworks of patients with glaucoma have a higher hardness than people in the control group. As an important component of the aqueous humor outflow channel, the state of the trabecular meshwork can have a direct impact on intraocular tension. The hardness of trabecular meshwork may be an important determinant of optic nerve damage in patients with glaucoma. Therefore, it is of great significance to find novel lncRNA molecules related to trabecular meshwork calcification for future glaucoma-related therapies.

What is claimed is:

1. A preparation comprising a siRNA targeted to lncRNAs ENST00000607393 (SEQ ID NO:1), for use in a method for treating glaucoma.

2. The preparation according to claim 1, wherein the method for treating glaucoma comprises: a positive-sense strand sequence of 5'-GCAGGCGUGUGCAUUUCUU-3' (SEQ ID NO: 2), and an antisense strand sequence of 5'-AAGAAAUGCACACGCCUGC-3' (SEQ ID NO: 3) of the siRNA targeted to ENST00000607393.

3. The preparation according to claim 1, wherein the method for treating glaucoma comprises: a negative control comprising a positive-sense strand sequence of 5'-UUCUCCGAACGUGUCACGU-3' (SEQ ID NO: 4), and an antisense strand sequence of 5'-ACGUGACACGUUCGGAGAA-3' (SEQ ID NO: 5).

* * * * *

SEQUENCE LISTING

<160> NUMBER OF SEQ ID NOS: 8

<210> SEQ ID NO 1
<211> LENGTH: 312
<212> TYPE: DNA
<213> ORGANISM: Artificial sequence
<220> FEATURE:
<223> OTHER INFORMATION: Sequence of lncRNA: ENST00000607393

<400> SEQUENCE: 1

```
ctagcttccg agggacttct ctgcgagcac cgcaggcgtg tgcatttctt cgaatctgag    60
aattccagcg aactcgggct ctaccagagt ttaagtcggc ccctggggcg tctgtttgtt   120
tattggctct taagggaaaa aagtttgaag atctttaacc agcctcagac ctggcgcggg   180
cggaaatccc ggaatctccc caagcaaaag tgatataact tcaagtcgtt atataagtgg   240
ggggctcctt cttcccctcc ctacgccgag ccttctcatt atcattccgg gagtaaaatg   300
tgtctcgctc aa                                                       312
```

<210> SEQ ID NO 2
<211> LENGTH: 19
<212> TYPE: RNA
<213> ORGANISM: Artificial sequence
<220> FEATURE:
<223> OTHER INFORMATION: Positive-sense strand sequence of siRNA against
      ENST00000607393

<400> SEQUENCE: 2

```
gcaggcgugu gcauuucuu                                                 19
```

<210> SEQ ID NO 3
<211> LENGTH: 19
<212> TYPE: RNA
<213> ORGANISM: Artificial sequence
<220> FEATURE:
<223> OTHER INFORMATION: Antisense strand sequence of siRNA against
      ENST00000607393

<400> SEQUENCE: 3

```
aagaaaugca cacgccugc                                                 19
```

<210> SEQ ID NO 4
<211> LENGTH: 19
<212> TYPE: RNA
<213> ORGANISM: Artificial sequence
<220> FEATURE:
<223> OTHER INFORMATION: Positive-sense strand sequence of negative
      control

<400> SEQUENCE: 4

```
uucuccgaac gugucacgu                                                 19
```

<210> SEQ ID NO 5
<211> LENGTH: 19
<212> TYPE: RNA
<213> ORGANISM: Artificial sequence
<220> FEATURE:
<223> OTHER INFORMATION: Antisense strand sequence of negative control

<400> SEQUENCE: 5

```
acgugacacg uucggagaa                                             19

<210> SEQ ID NO 6
<211> LENGTH: 19
<212> TYPE: DNA
<213> ORGANISM: Artificial sequence
<220> FEATURE:
<223> OTHER INFORMATION: FISH probe 1

<400> SEQUENCE: 6
agaaggctcg gcgtaggga                                             19

<210> SEQ ID NO 7
<211> LENGTH: 23
<212> TYPE: DNA
<213> ORGANISM: Artificial sequence
<220> FEATURE:
<223> OTHER INFORMATION: FISH probe 2

<400> SEQUENCE: 7
tgataatgag aaggctcggc gta                                        23

<210> SEQ ID NO 8
<211> LENGTH: 20
<212> TYPE: DNA
<213> ORGANISM: Artificial sequence
<220> FEATURE:
<223> OTHER INFORMATION: FISH probe 3

<400> SEQUENCE: 8
gagcccgagt tcgctggaat                                            20
```